(12) United States Patent
Liu et al.

(10) Patent No.: US 12,019,193 B2
(45) Date of Patent: Jun. 25, 2024

(54) IMAGING SYSTEM

(71) Applicant: SHENZHEN XPECTVISION TECHNOLOGY CO., LTD., Shenzhen (CN)

(72) Inventors: Yurun Liu, Shenzhen (CN); Peiyan Cao, Shenzhen (CN)

(73) Assignee: SHENZHEN XPECTVISION TECHNOLOGY CO., LTD., Shenzhen (CN)

( * ) Notice: Subject to any disclaimer, the term of this patent is extended or adjusted under 35 U.S.C. 154(b) by 203 days.

(21) Appl. No.: 17/863,709

(22) Filed: Jul. 13, 2022

(65) Prior Publication Data

US 2022/0350038 A1 Nov. 3, 2022

Related U.S. Application Data

(63) Continuation of application No. PCT/CN2020/076915, filed on Feb. 27, 2020.

(51) Int. Cl.
*G01T 1/17* (2006.01)
*G01N 23/04* (2018.01)
*G01T 7/00* (2006.01)

(52) U.S. Cl.
CPC ............. *G01T 1/17* (2013.01); *G01N 23/04* (2013.01); *G01T 7/00* (2013.01)

(58) Field of Classification Search
CPC .............. G01N 23/04; G01T 1/17; G01T 7/00
See application file for complete search history.

(56) References Cited

U.S. PATENT DOCUMENTS

| | | | | |
|---|---|---|---|---|
| 5,394,342 A | * | 2/1995 | Poon | B27B 1/007 382/110 |
| 5,410,156 A | * | 4/1995 | Miller | G01N 23/09 250/390.11 |
| 5,693,947 A | * | 12/1997 | Morton | G01T 1/185 250/370.09 |
| 5,847,398 A | * | 12/1998 | Shahar | G01T 1/243 250/370.09 |
| 6,038,282 A | * | 3/2000 | Wiesent | A61B 6/4441 378/62 |
| 6,196,715 B1 | | 3/2001 | Nambu et al. | |
| 6,272,207 B1 | * | 8/2001 | Tang | G21K 1/025 378/154 |
| 6,529,622 B1 | * | 3/2003 | Pourjavid | H04N 25/68 348/E5.081 |
| 2004/0013225 A1 | | 1/2004 | Gregerson et al. | |
| 2006/0165211 A1 | | 7/2006 | Goto et al. | |
| 2007/0058774 A1 | | 3/2007 | Ramsauer | |

(Continued)

FOREIGN PATENT DOCUMENTS

| | | |
|---|---|---|
| CN | 108338802 A | 7/2018 |
| TW | 201713966 A | 4/2017 |
| WO | 2020019285 A1 | 1/2020 |

*Primary Examiner* — Blake C Riddick
(74) *Attorney, Agent, or Firm* — IPRO, PLLC

(57) ABSTRACT

Disclosed herein is a method comprising: translating a detector module such that a point of the detector module moves along a curve through movement rounds (i), i=1, . . . , M, with M being a positive integer, wherein the curve is smooth; and in the movement round (i), i=1, . . . , M, capturing partial images (i, j) of a scene using the detector module, j=1, . . . , Hi, when the point is at position Pi,j on the curve, with Hi being an integer greater than 1.

26 Claims, 11 Drawing Sheets

(56) References Cited

U.S. PATENT DOCUMENTS

| | | |
|---|---|---|
| 2007/0140408 A1 | 6/2007 | Takiura et al. |
| 2008/0135757 A1* | 6/2008 | D'Souza .............. G01J 3/2803 250/332 |
| 2008/0224061 A1 | 9/2008 | Smith |
| 2009/0003515 A1* | 1/2009 | Naidu .................. G01V 5/226 378/14 |
| 2009/0252285 A1* | 10/2009 | Shapiro ................ A61B 6/032 378/8 |
| 2009/0257551 A1* | 10/2009 | Dafni ................... A61B 6/4014 378/9 |
| 2009/0304142 A1* | 12/2009 | Ruimi .................. A61B 6/032 378/7 |
| 2010/0172563 A1 | 7/2010 | Hagiwara |
| 2010/0329534 A1 | 12/2010 | Biermann et al. |
| 2011/0007878 A1* | 1/2011 | Dafni ................... G01T 1/2985 250/505.1 |
| 2011/0064190 A1* | 3/2011 | Ruimi .................. A61B 6/5282 378/154 |
| 2012/0307963 A1 | 12/2012 | Watanabe et al. |
| 2014/0139684 A1* | 5/2014 | Binder .................. H04N 5/33 348/164 |
| 2015/0146957 A1* | 5/2015 | Katsevich ............ A61B 6/032 382/131 |
| 2016/0163754 A1* | 6/2016 | Igarashi ............ H01L 27/14663 438/69 |
| 2016/0249869 A1 | 9/2016 | Papalazarou et al. |
| 2017/0077186 A1* | 3/2017 | Tallal ................... H10K 39/36 |
| 2017/0229502 A1* | 8/2017 | Liu .................. H01L 27/14676 |
| 2018/0255212 A1* | 9/2018 | Sprigg .................. H04N 23/81 |
| 2018/0368791 A1 | 12/2018 | Nig et al. |
| 2020/0222016 A1* | 7/2020 | Pan ....................... A61B 6/405 |
| 2021/0228167 A1* | 7/2021 | Kanda .................. G06T 11/006 |
| 2021/0262947 A1* | 8/2021 | Takanashi ............. G01N 21/17 |

\* cited by examiner

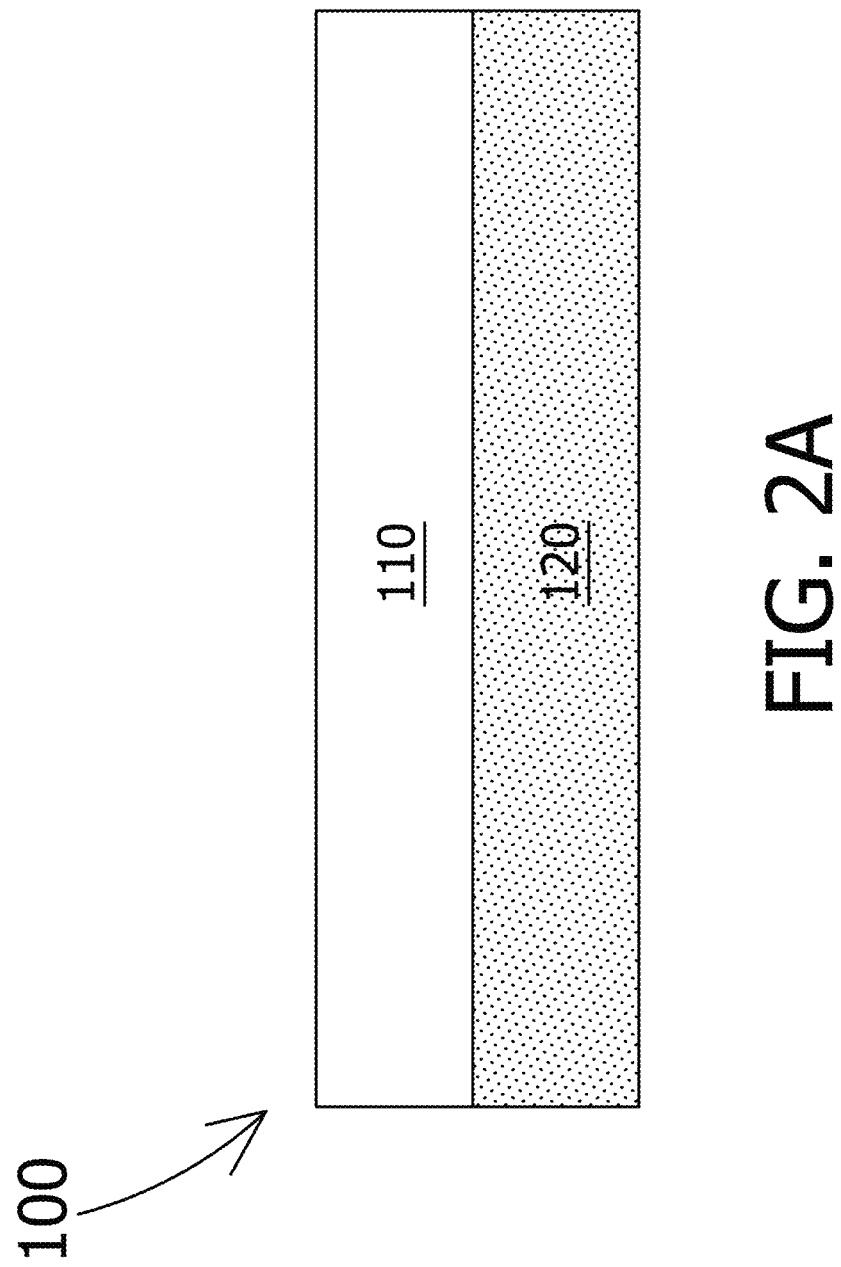

IMAGING SYSTEM

BACKGROUND

A radiation detector is a device that measures a property of a radiation. Examples of the property may include a spatial distribution of the intensity, phase, and polarization of the radiation. The radiation may be one that has interacted with an object. For example, the radiation measured by the radiation detector may be a radiation that has penetrated the object. The radiation may be an electromagnetic radiation such as infrared light, visible light, ultraviolet light, X-ray or γ-ray. The radiation may be of other types such as α-rays and β-rays. An imaging system may include multiple radiation detectors.

SUMMARY

Disclosed herein is a method comprising: translating a detector module such that a point of the detector module moves along a curve through movement rounds (i), i=1, . . . , M, with M being a positive integer, wherein the curve is smooth; and in the movement round (i), i=1, . . . , M, capturing partial images (i, j) of a scene using the detector module, j=1, . . . , $H_i$, when the point is at position $P_{i,j}$ on the curve, with $H_i$ being an integer greater than 1.

In an aspect, the curve is a circle.

In an aspect, the curve comprises a straight line segment, and the positions $P_{i,j}$ are on the straight line segment.

In an aspect, M≥2.

In an aspect, the detector module comprises N spatially discontinuous active areas, N being a positive integer greater than 1.

In an aspect, velocity of the point is a continuous function of time through the movement rounds (i), i=1, . . . , M.

In an aspect, capturing partial image (i, j) comprises gathering charge carriers generated in detector module in response to incident radiation when the point is at position $P_{i,j}$ in the movement round (i).

In an aspect, the detector module comprises N spatially discontinuous active areas arranged in K rows and L columns, with K, L, and N being positive integers, and the K rows define a row direction and the L columns define a column direction.

In an aspect, a size in the row direction of one of the N spatially discontinuous active areas is greater than a distance between two neighboring active areas of the N spatially discontinuous active areas in a row of the K rows, and a size in the column direction of one of the N spatially discontinuous active areas is greater than a distance between two neighboring active areas of the N spatially discontinuous active areas in a column of the L columns.

In an aspect, the method further comprises operating a shield system such that the shield system blocks radiation not targeting the N spatially discontinuous active areas while the point is at the positions $P_{i,j}$, i=1, . . . , M and j=1, . . . , $H_i$.

In an aspect, the shield system comprises (A) row shield bars extending in the row direction and (B) column shield bars extending in the column direction, and operating the shield system comprises translating the row shield bars along the column direction, translating the column shield bars along the row direction, or both.

In an aspect, the method further comprises, for the movement round (i), forming an image (i) of an entirety of the scene by stitching the partial images (i, j), j=1, . . . , $H_i$.

In an aspect, the curve is closed.

Disclosed herein is an imaging system, comprising a detector module, wherein the imaging system is configured to translate the detector module such that a point of the detector module moves along a curve through movement rounds (i), i=1, . . . , M, with M being a positive integer, wherein the curve is smooth, and wherein in the movement round (i), the detector module is configured to capture partial images (i, j) of a scene when the point is at positions $P_{i,j}$ on the curve, with $H_i$ being an integer greater than 1.

In an aspect, the curve is a circle.

In an aspect, the curve comprises a straight line segment, and the $H_i$ positions are on the straight line segment.

In an aspect, M≥2.

In an aspect, the detector module comprises N spatially discontinuous active areas, N being a positive integer greater than 1.

In an aspect, velocity of the point is a continuous function of time through the movement rounds (i), i=1, . . . , M.

In an aspect, the detector module is configured to capture partial image (i, j) by gathering charge carriers generated in the detector module in response to incident radiation when the point is at position $P_{i,j}$.

In an aspect, the detector module comprises N spatially discontinuous active areas arranged in K rows and L columns, with K, L, and N being positive integers, and the K rows define a row direction and the L columns define a column direction.

In an aspect, a size in the row direction of one of the N spatially discontinuous active areas is greater than a distance between two neighboring active areas of the N spatially discontinuous active areas in a row of the K rows, and a size in the column direction of one of the N spatially discontinuous active areas is greater than a distance between two neighboring active areas of the N spatially discontinuous active areas in a column of the L columns.

In an aspect, the imaging system further comprises a shield system configured to block radiation not targeting the N spatially discontinuous active areas while the point is at the positions $P_{i,j}$, i=1, . . . , M and j=1, . . . , $H_i$.

In an aspect, the shield system comprises (A) row shield bars extending in the row direction and (B) column shield bars extending in the column direction, and the shield system is configured to translate the row shield bars along the column direction, translate the column shield bars along the row direction, or both.

In an aspect, the imaging system further comprises a processor configured to, for the movement round (i), form an image (i) of an entirety of the scene by stitching the partial images (i, j), j=1, . . . , $H_i$.

In an aspect, the curve is closed.

BRIEF DESCRIPTION OF FIGURES

FIG. 2A schematically shows a simplified cross-sectional view of the radiation detector.

DETAILED DESCRIPTION

Figure 1:
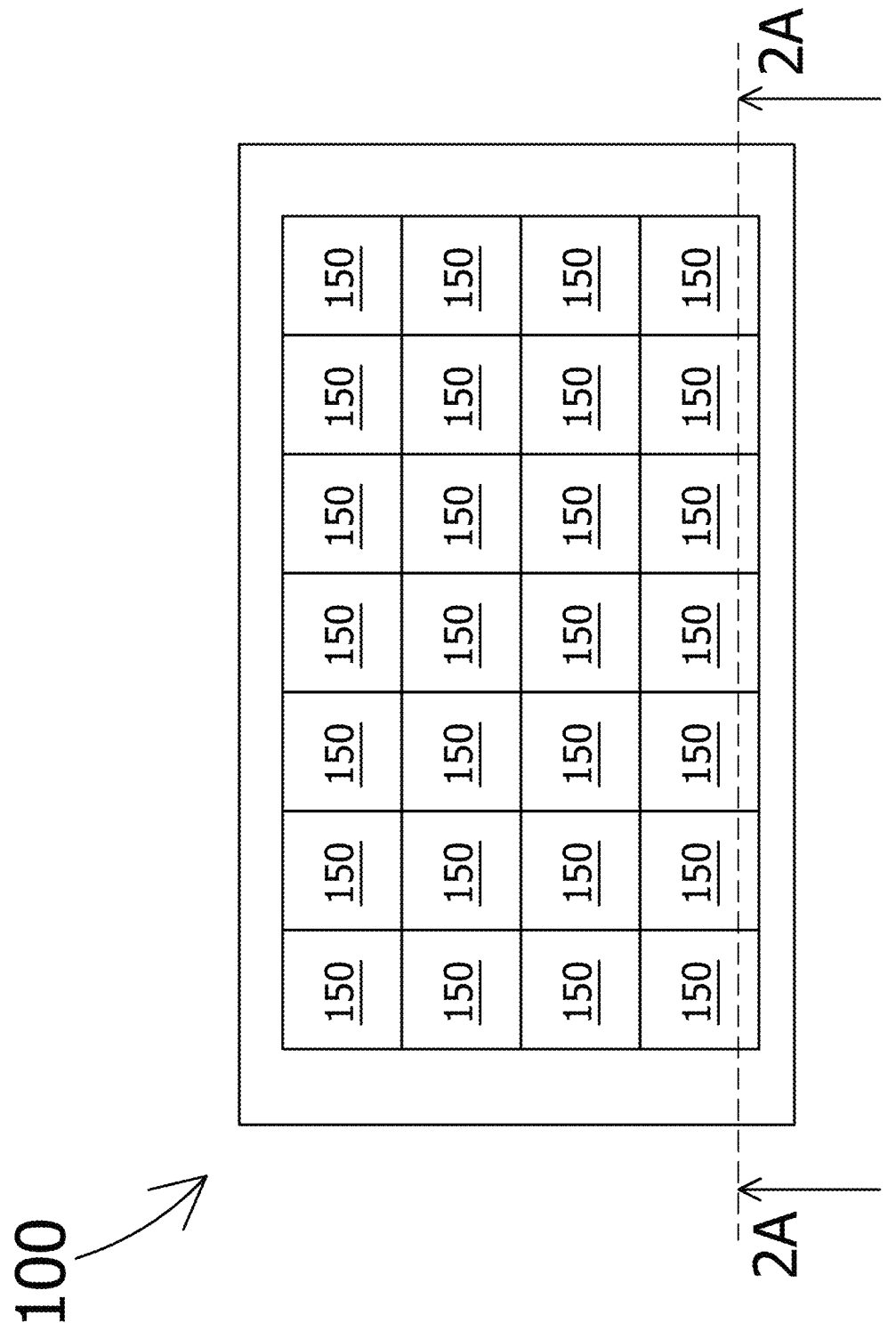
FIG. 1 schematically shows a radiation detector, according to an embodiment.

FIG. 1 schematically shows a radiation detector 100, as an example. The radiation detector 100 may include an array of pixels 150 (also referred to as sensing elements 150). The array may be a rectangular array (as shown in FIG. 1), a honeycomb array, a hexagonal array or any other suitable array. The array of pixels 150 in the example of FIG. 1 has 28 pixels 150 arranged in 4 rows and 7 columns; in general, the array of pixels 150 may have any number of pixels 150 arranged in any way.

A radiation may include particles such as photons (electromagnetic waves) and subatomic particles (e.g., neutrons, protons, electrons, alpha particles, etc.) Each pixel 150 may be configured to detect radiation incident thereon and may be configured to measure a characteristic (e.g., the energy of the particles, the wavelength, and the frequency) of the incident radiation. The measurement results for the pixels 150 of the radiation detector 100 constitute an image of the radiation incident on the pixels. It may be said that the image is of an object or a scene which the incident radiation come from.

Each pixel 150 may be configured to count numbers of particles of radiation incident thereon whose energy falls in a plurality of bins of energy, within a period of time. All the pixels 150 may be configured to count the numbers of particles of radiation incident thereon within a plurality of bins of energy within the same period of time. When the incident particles of radiation have similar energy, the pixels 150 may be simply configured to count numbers of particles of radiation incident thereon within a period of time, without measuring the energy of the individual particles of radiation.

Each pixel 150 may have its own analog-to-digital converter (ADC) configured to digitize an analog signal representing the energy of an incident particle of radiation into a digital signal, or to digitize an analog signal representing the total energy of a plurality of incident particles of radiation into a digital signal. The pixels 150 may be configured to operate in parallel. For example, when one pixel 150 measures an incident particle of radiation, another pixel 150 may be waiting for a particle of radiation to arrive. The pixels 150 may not have to be individually addressable.

The radiation detector 100 described here may have applications such as in an X-ray telescope, X-ray mammography, industrial X-ray defect detection, X-ray microscopy or microradiography, X-ray casting inspection, X-ray non-destructive testing, X-ray weld inspection, X-ray digital subtraction angiography, etc. It may be suitable to use this radiation detector 100 in place of a photographic plate, a photographic film, a PSP plate, an X-ray image intensifier, a scintillator, or another semiconductor X-ray detector.

FIG. 2A schematically shows a simplified cross-sectional view of the radiation detector 100 of FIG. 1 along a line 2A-2A, according to an embodiment. More specifically, the radiation detector 100 may include a radiation absorption layer 110 and an electronics layer 120 (e.g., an ASIC) for processing or analyzing electrical signals which incident radiation generates in the radiation absorption layer 110. The radiation detector 100 may or may not include a scintillator (not shown). The radiation absorption layer 110 may comprise a semiconductor material such as silicon, germanium, GaAs, CdTe, CdZnTe, or a combination thereof. The semiconductor material may have a high mass attenuation coefficient for the radiation of interest.

Figure 2B:
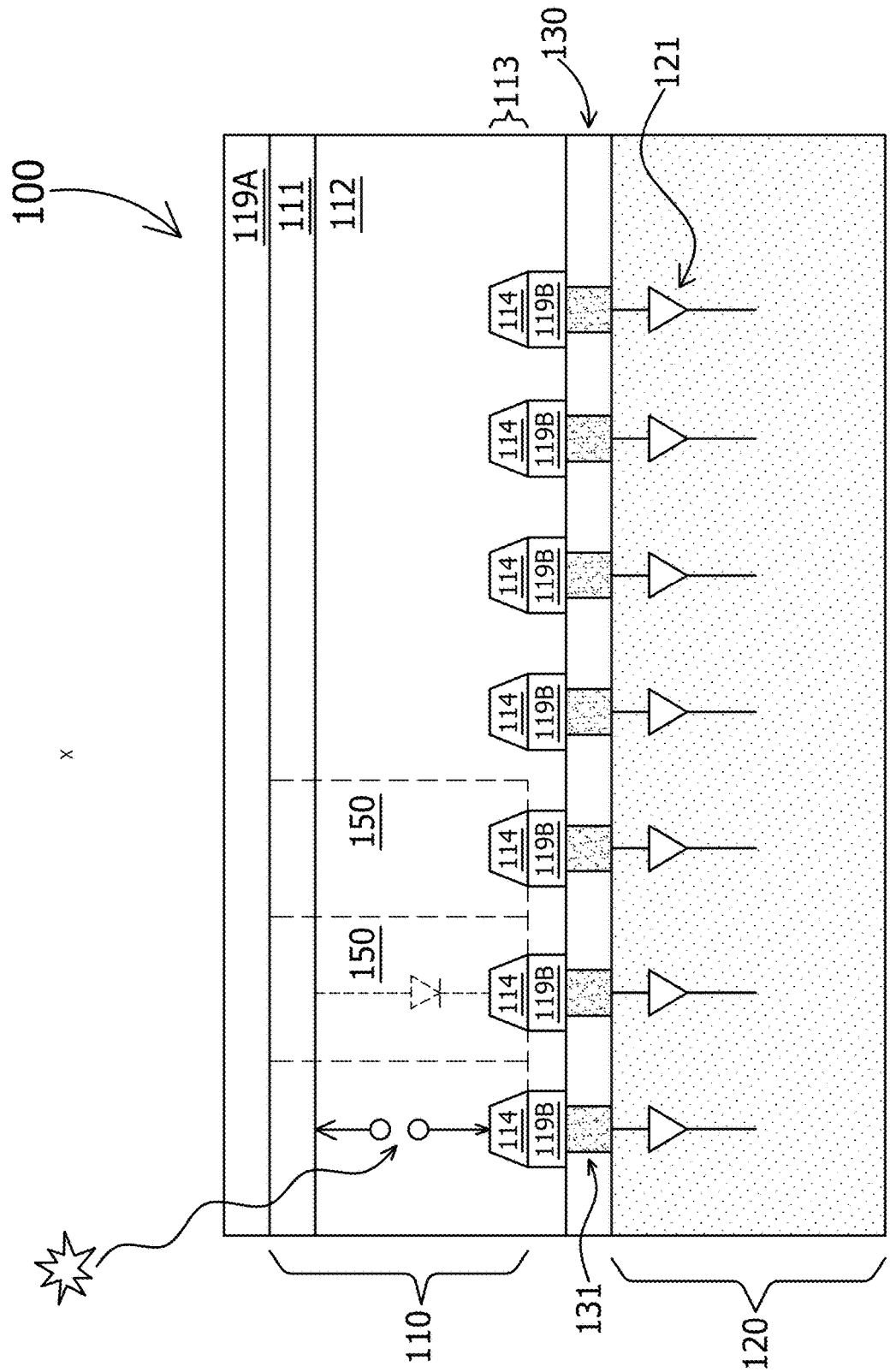
FIG. 2B schematically shows a detailed cross-sectional view of the radiation detector.

FIG. 2B schematically shows a detailed cross-sectional view of the radiation detector 100 of FIG. 1 along the line 2A-2A, as an example. More specifically, the radiation absorption layer 110 may include one or more diodes (e.g., p-i-n or p-n) formed by a first doped region 111 and one or more discrete regions 114 of a second doped region 113. The second doped region 113 may be separated from the first doped region 111 by an optional intrinsic region 112. The discrete regions 114 are separated from one another by the first doped region 111 or the intrinsic region 112. The first doped region 111 and the second doped region 113 have opposite types of doping (e.g., region 111 is p-type and region 113 is n-type, or region 111 is n-type and region 113 is p-type). In the example of FIG. 2B, each of the discrete regions 114 of the second doped region 113 forms a diode with the first doped region 111 and the optional intrinsic region 112. Namely, in the example in FIG. 2B, the radiation absorption layer 110 has a plurality of diodes (more specifically, FIG. 2B shows 7 diodes corresponding to 7 pixels 150 of one row in the array of FIG. 1, of which only 2 pixels 150 are labeled in FIG. 2B for simplicity). The plurality of diodes have an electrode 119A as a shared (common) electrode. The first doped region 111 may also have discrete portions.

The electronics layer 120 may include an electronic system 121 suitable for processing or interpreting signals generated by the radiation incident on the radiation absorption layer 110. The electronic system 121 may include an analog circuitry such as a filter network, amplifiers, integrators, and comparators, or a digital circuitry such as a microprocessor, and memory. The electronic system 121 may include one or more ADCs. The electronic system 121 may include components shared by the pixels 150 or components dedicated to a single pixel 150. For example, the electronic system 121 may include an amplifier dedicated to each pixel 150 and a microprocessor shared among all the pixels 150. The electronic system 121 may be electrically connected to the pixels 150 by vias 131. Space among the vias may be filled with a filler material 130, which may increase the mechanical stability of the connection of the electronics layer 120 to the radiation absorption layer 110. Other bonding techniques are possible to connect the electronic system 121 to the pixels 150 without using the vias 131.

When radiation from the radiation source (not shown) hits the radiation absorption layer 110 including diodes, particles of the radiation may be absorbed and generate one or more charge carriers (e.g., electrons, holes) by a number of mechanisms. The charge carriers may drift to the electrodes of one of the diodes under an electric field. The field may be an external electric field. The electrical contact 119B may include discrete portions each of which is in electrical contact with the discrete regions 114. The term "electrical contact" may be used interchangeably with the word "electrode." In an embodiment, the charge carriers may drift in directions such that the charge carriers generated by a single particle of the radiation are not substantially shared by two different discrete regions 114 ("not substantially shared" here means less than 2%, less than 0.5%, less than 0.1%, or less than 0.01% of these charge carriers flow to a different one of the discrete regions 114 than the rest of the charge carriers). Charge carriers generated by a particle of the radiation incident around the footprint of one of these discrete regions 114 are not substantially shared with another of these discrete regions 114. A pixel 150 associated with a discrete region 114 may be a space around the discrete region 114 in which substantially all (more than 98%, more than 99.5%, more than 99.9%, or more than 99.99% of) charge carriers generated by a particle of the radiation incident therein flow to the discrete region 114. Namely, less than 2%, less than 1%, less than 0.1%, or less than 0.01% of these charge carriers flow beyond the pixel 150.

Figure 2C:
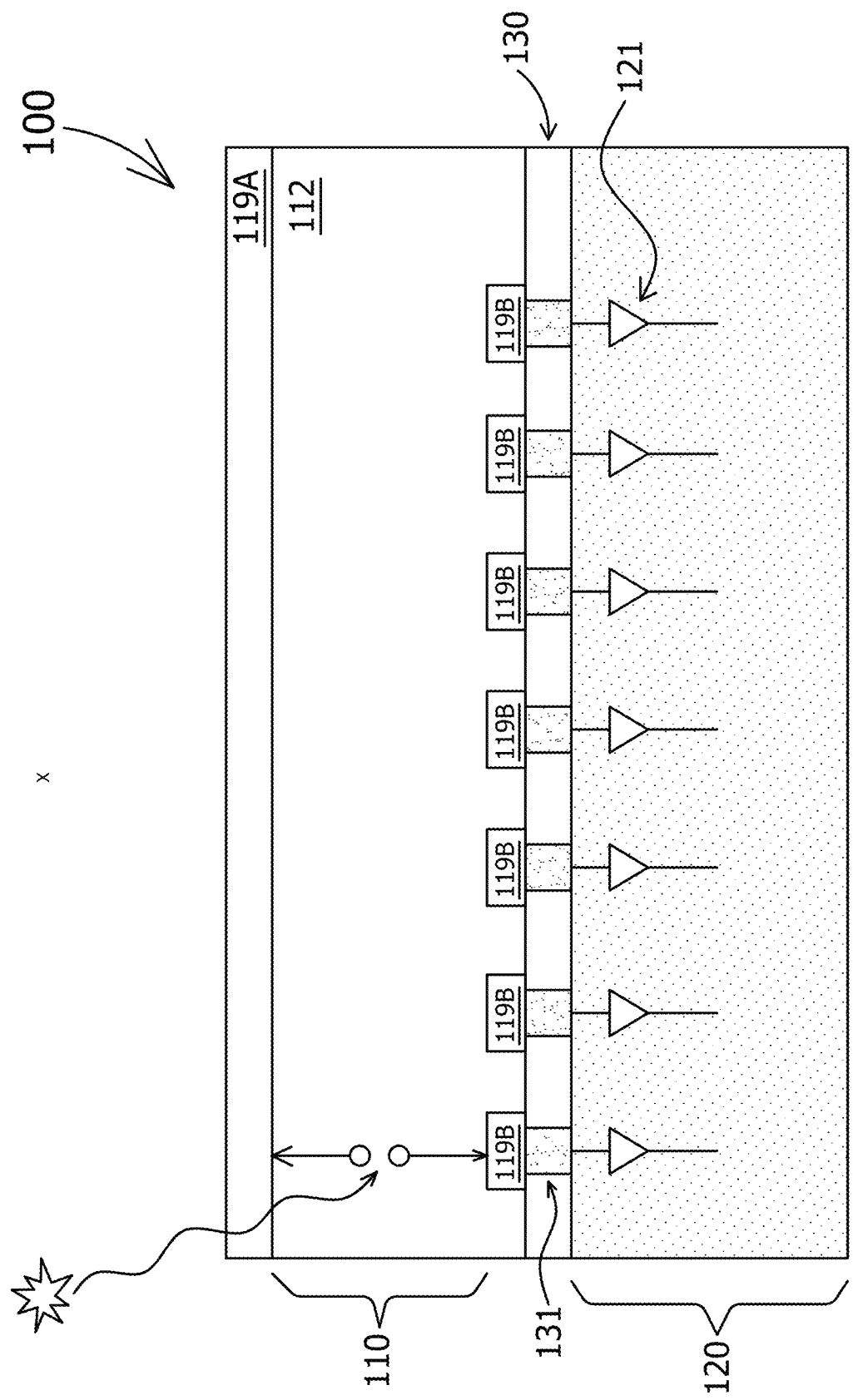
FIG. 2C schematically shows an alternative detailed cross-sectional view of the radiation detector.

FIG. 2C schematically shows an alternative detailed cross-sectional view of the radiation detector 100 of FIG. 1 along the line 2A-2A, according to an embodiment. More specifically, the radiation absorption layer 110 may include a resistor of a semiconductor material such as silicon, germanium, GaAs, CdTe, CdZnTe, or a combination thereof, but does not include a diode. The semiconductor material may have a high mass attenuation coefficient for the radiation of interest. In an embodiment, the electronics layer 120 of FIG. 2C may be similar to the electronics layer 120 of FIG. 2B in terms of structure and function.

When the radiation hits the radiation absorption layer 110 including the resistor but not diodes, it may be absorbed and generate one or more charge carriers by a number of mechanisms. A particle of the radiation may generate 10 to 100,000 charge carriers. The charge carriers may drift to the electrical contacts 119A and 119B under an electric field. The electric field may be an external electric field. The electrical contact 119B includes discrete portions. In an embodiment, the charge carriers may drift in directions such that the charge carriers generated by a single particle of the radiation are not substantially shared by two different discrete portions of the electrical contact 119B ("not substantially shared" here means less than 2%, less than 0.5%, less than 0.1%, or less than 0.01% of these charge carriers flow to a different one of the discrete portions than the rest of the charge carriers). Charge carriers generated by a particle of the radiation incident around the footprint of one of these discrete portions of the electrical contact 119B are not substantially shared with another of these discrete portions of the electrical contact 119B. A pixel 150 associated with a discrete portion of the electrical contact 119B may be a space around the discrete portion in which substantially all (more than 98%, more than 99.5%, more than 99.9% or more than 99.99% of) charge carriers generated by a particle of the radiation incident therein flow to the discrete portion of the electrical contact 119B. Namely, less than 2%, less than 0.5%, less than 0.1%, or less than 0.01% of these charge carriers flow beyond the pixel associated with the one discrete portion of the electrical contact 119B.

Figure 3:
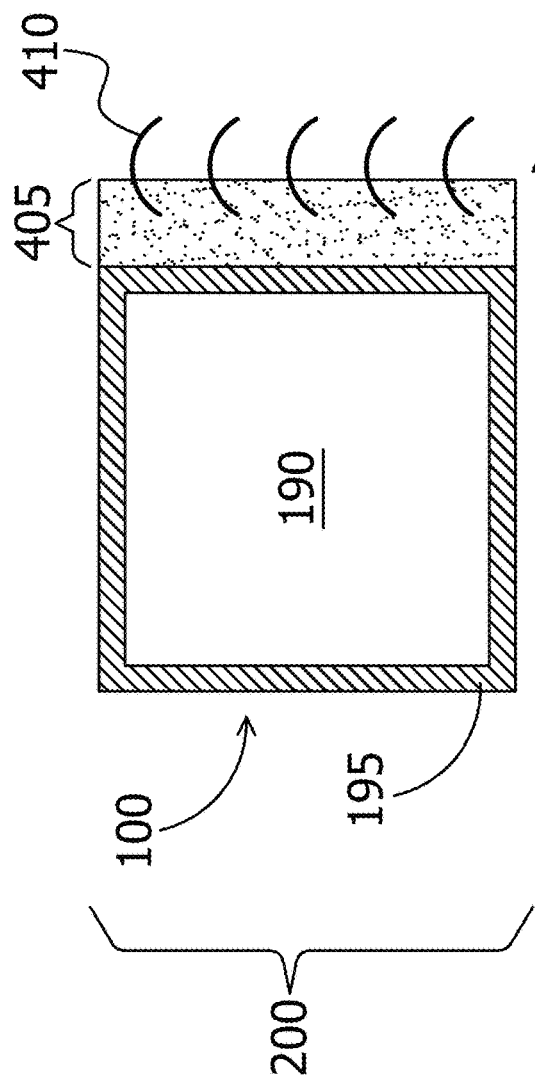
FIG. 3 schematically shows a top view of a package including the radiation detector and a printed circuit board (PCB).

FIG. 3 schematically shows a top view of a package 200 including the radiation detector 100 and a printed circuit board (PCB) 400. The term "PCB" as used herein is not limited to a particular material. For example, a PCB may comprise a semiconductor. The radiation detector 100 may be mounted to the PCB 400. The wiring between the radiation detector 100 and the PCB 400 is not shown for the sake of clarity. The PCB 400 may have one or more radiation detectors 100. The PCB 400 may have an area 405 not covered by the radiation detector 100 (e.g., for accommodating bonding wires 410). The radiation detector 100 may have an active area 190, which is where the pixels 150 (FIG. 1) are located. The radiation detector 100 may have a perimeter zone 195 near the edges of the radiation detector 100. The perimeter zone 195 has no pixels 150, and the radiation detector 100 does not detect particles of radiation incident on the perimeter zone 195.

Figure 4:
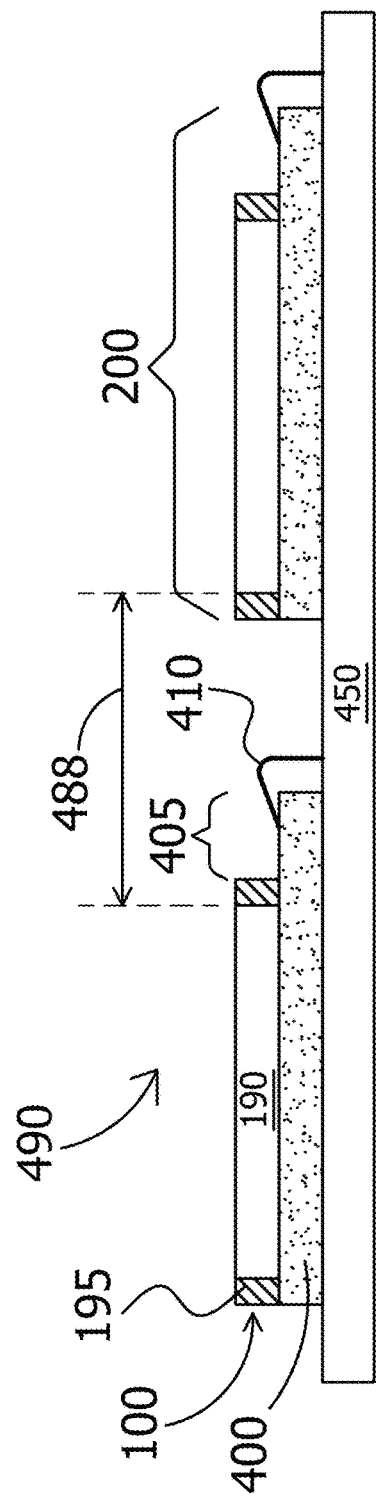
FIG. 4 schematically shows a cross-sectional view of a detector module, where a plurality of the packages of FIG. 3 are mounted to a system PCB, according to an embodiment.

FIG. 4 schematically shows a cross-sectional view of a detector module 490, according to an embodiment. The detector module 490 may include one or a plurality of the packages 200 of FIG. 3 mounted to a system PCB 450. FIG. 4 shows only 2 packages 200 as an example. The electrical connection between the PCBs 400 and the system PCB 450 may be made by bonding wires 410. In order to accommodate the bonding wires 410 on the PCB 400, the PCB 400 may have the area 405 not covered by the radiation detector 100. In order to accommodate the bonding wires 410 on the system PCB 450, the packages 200 may have gaps in between. The gaps may be approximately 1 mm or more. Particles of radiation incident on the perimeter zones 195, on the area 405, or on the gaps cannot be detected by the packages 200 on the system PCB 450.

A dead zone of a radiation detector (e.g., the radiation detector 100) is the area of the radiation-receiving surface of the radiation detector, in which incident particles of radiation cannot be detected by the radiation detector. A dead zone of a package (e.g., package 200) is the area of the radiation-receiving surface of the package, in which incident particles of radiation cannot be detected by the detector or detectors in the package. In this example shown in FIG. 3 and FIG. 4, the dead zone of the package 200 includes the perimeter zones 195 and the area 405. A dead zone (e.g., 488) of a detector module (e.g., detector module 490) with a group of packages (e.g., packages mounted on the same PCB, packages arranged in the same layer) includes the combination of the dead zones of the packages in the group and the gaps among the packages.

In an embodiment, the detector module 490 including the radiation detectors 100 may have the dead zone 488 incapable of detecting incident radiation. However, in an embodiment, the detector module 490 with spatially discontinuous active areas 190 may capture partial images of incident radiation. In an embodiment, these captured partial images are such that they can be stitched by the detector module 490 (e.g., a processor thereof) to form a single image of incident radiation. In other words, these captured partial images are such that it is possible to stitch these captured partial images to form a single image. In an embodiment, these captured partial images may be stitched to form a single image.

FIG. 5A-FIG. 5D schematically show top views of the detector module 490 in operation, according to an embodiment. In an embodiment, the detector module 490 may comprise 2 active areas 190a and 190b (similar to active areas 190 of FIG. 3 and FIG. 4) and the dead zone 488. For simplicity, other parts of the detector module 490 such as perimeter zones 195 (FIG. 4) are not shown. In an embodiment, a cardboard box 510 enclosing a metal sword 512 may be positioned between the detector module 490 and a radiation source (not shown) which is before the page. The cardboard box 510 is between the detector module 490 and the eye of viewer. Hereafter, for generalization, the cardboard box 510 enclosing the metal sword 512 may be referred to as the object or scene 510+512.

Figure 5:
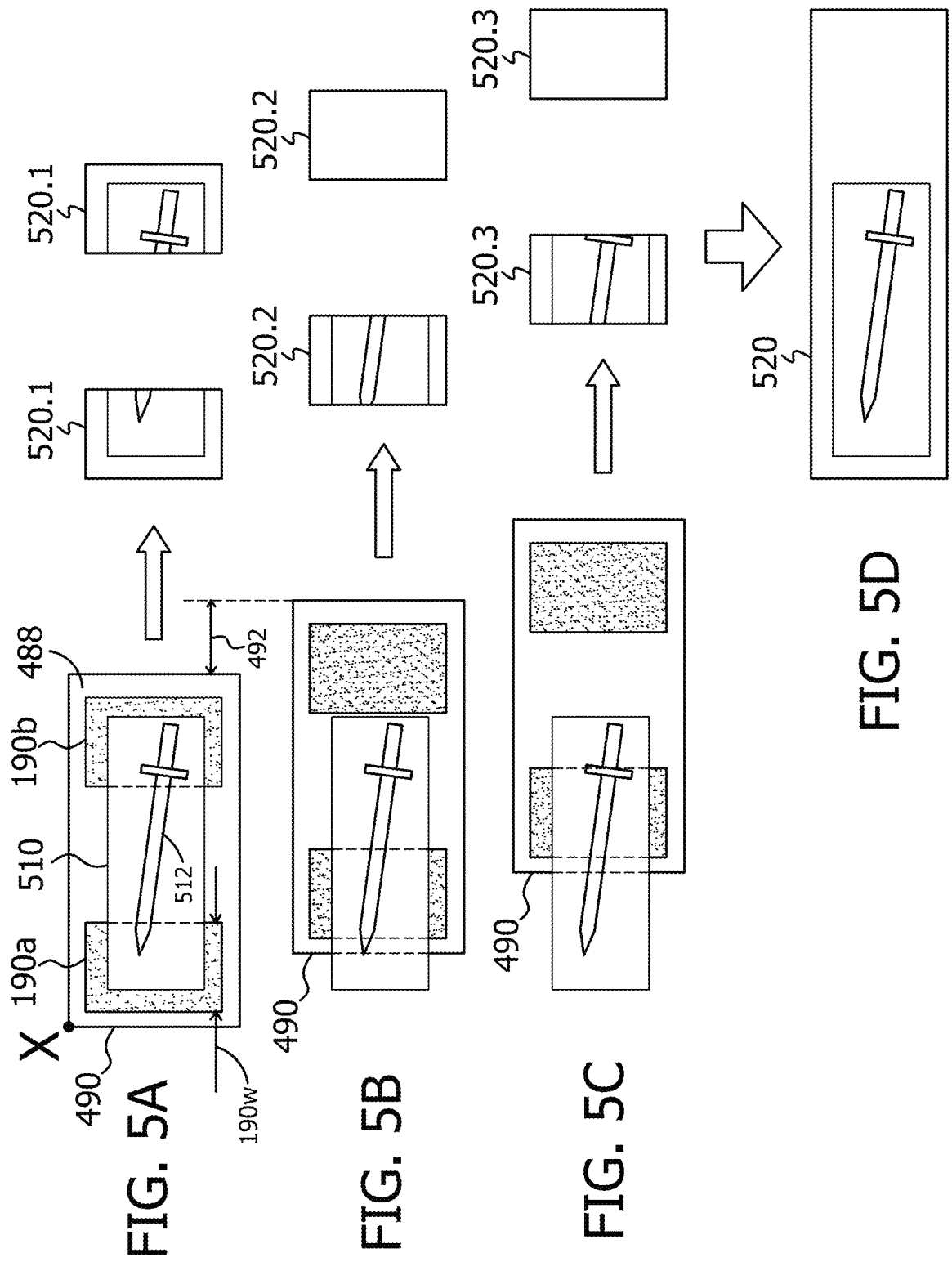
FIG. 5A-FIG. 5D schematically show top views of the detector module in operation, according to an embodiment.

In an embodiment, the operation of the detector module 490 in capturing images of the object/scene 510+512 may be as follows. Firstly, the object/scene 510+512 may be stationary, and the detector module 490 may be moved to a first imaging position relative to the object/scene 510+512 as shown in FIG. 5A. Then, the detector module 490 (specifically, the active areas 190a and 190b) may be used to capture a first partial image 520.1 of the object/scene 510+512 while the detector module 490 is at the first imaging position.

Next, in an embodiment, the detector module 490 may be moved to a second imaging position relative to the object/scene 510+512 as shown in FIG. 5B. Then, the detector module 490 (specifically, the active areas 190a and 190b) may be used to capture a second partial image 520.2 of the object/scene 510+512 while the detector module 490 is at the second imaging position.

Next, in an embodiment, the detector module 490 may be moved to a third imaging position relative to the object/scene 510+512 as shown in FIG. 5C. Then, the detector module 490 (specifically, the active areas 190a and 190b) may be used to capture a third partial image 520.3 of the object/scene 510+512 while the detector module 490 is at the third imaging position.

In an embodiment, the size and shape of the active areas 190a and 190b and the positions of the first, second, and third imaging positions may be such that any partial image of the partial images 520.1, 520.2, and 520.3 overlaps at least another partial image of the partial images 520.1, 520.2, and 520.3. For example, a distance 492 between the first and second imaging positions may be close to and less than a width 190w of the active area 190a; as a result, the first partial image 520.1 overlaps the second partial image 520.2.

With any partial image of the partial images 520.1, 520.2, and 520.3 overlapping at least another partial image of the partial images 520.1, 520.2, and 520.3, it is possible to stitch the partial images 520.1, 520.2, and 520.3 to form a single image 520 (FIG. 5D) of the object/scene 510+512. In an embodiment, the partial images 520.1, 520.2, and 520.3 may be stitched to form the single image 520 (FIG. 5D) of the object/scene 510+512.

Figure 6:
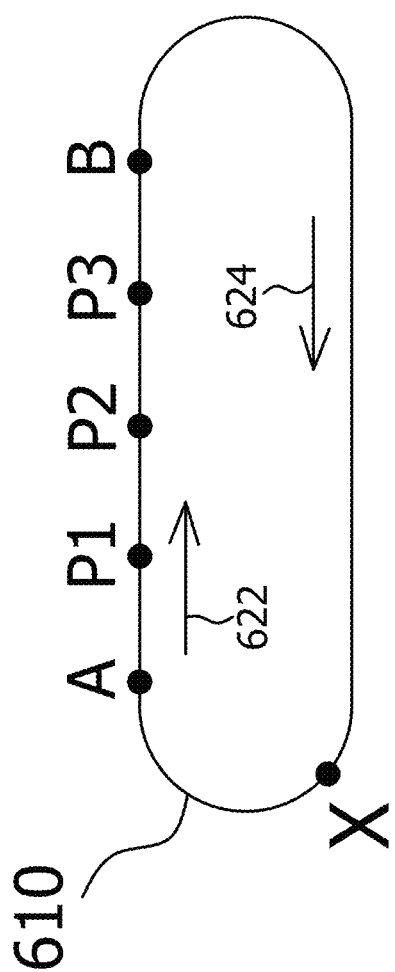
FIG. 6 schematically illustrates an operation of the detector module while a point of the detector module moves through movement rounds, according to an alternative embodiment.

FIG. 6 schematically illustrates an operation of the detector module 490 of FIG. 5A while a point X (FIG. 5A) of the detector module 490 moves through movement rounds, according to an alternative embodiment. The point X may be any point on the detector module 490 that is stationary relative to the detector module 490. Specifically, in an embodiment, in a first movement round of the point X, the detector module 490 may be translated (i.e., all points of the detector module 490 are simultaneously moved in the same direction by the same distance) such that the point X of the detector module 490 moves along a curve 610. In an embodiment, the point X may be at positions P1, P2, and P3 on the curve 610 when the detector module 490 is at the first, second, and third imaging positions (FIG. 5A-FIG. 5C) respectively.

In an embodiment, the curve 610 may be closed (i.e., the curve 610 has no end points and encloses an area) as shown. In an embodiment, the curve 610 may be smooth. A curve is smooth if and only if the curve is differentiable everywhere on the curve.

More specifically, in an embodiment, in the first movement round, the point X may start at a position A and move along the curve 610 in the direction 622 (i.e., clockwise). In an embodiment, when the point X is at the position P1, the detector module 490 may capture a fourth partial image (not shown). Next, in an embodiment, when the point X is at the position P2, the detector module 490 may capture a fifth partial image (not shown). Next, in an embodiment, when the point X is at the position P3, the detector module 490 may capture a sixth partial image (not shown). Next, in an embodiment, the point X may move along the curve 610 in the direction 624 (i.e., clockwise) back to the point A, completing the first movement round of the point X.

Next, in an embodiment, a second movement round of the point X may be performed. In an embodiment, the operation of the detector module 490 in the second movement round of the point X may be similar to the operation of the detector module 490 in the first movement round of the point X. Specifically, in an embodiment, in the second movement round, the point X may start at the position A and move along the curve 610 in the direction 622 (i.e., clockwise).

In an embodiment, when the point X is at the position P1, the detector module 490 may capture a seventh partial image (not shown). Next, in an embodiment, when the point X is at the position P2, the detector module 490 may capture an eighth partial image (not shown). Next, in an embodiment, when the point X is at the position P3, the detector module 490 may capture a ninth partial image (not shown). Next, in an embodiment, the point X may move along the curve 610 in the direction 624 (i.e., clockwise) back to the point A, completing the second movement round of the point X. However, in the second movement round, the point X may move along a curve different from the curve 610. In the second movement round, partial images may be captured when the point X are at positions other than P1, P2 and P3.

Next, in an embodiment, additional movement rounds of the point X similar to the first movement round of the point X may be performed. In an embodiment, the operation of the detector module 490 in each of the additional movement rounds of the point X may be similar to the operation of the detector module 490 in the first movement round of the point X.

Figure 7:
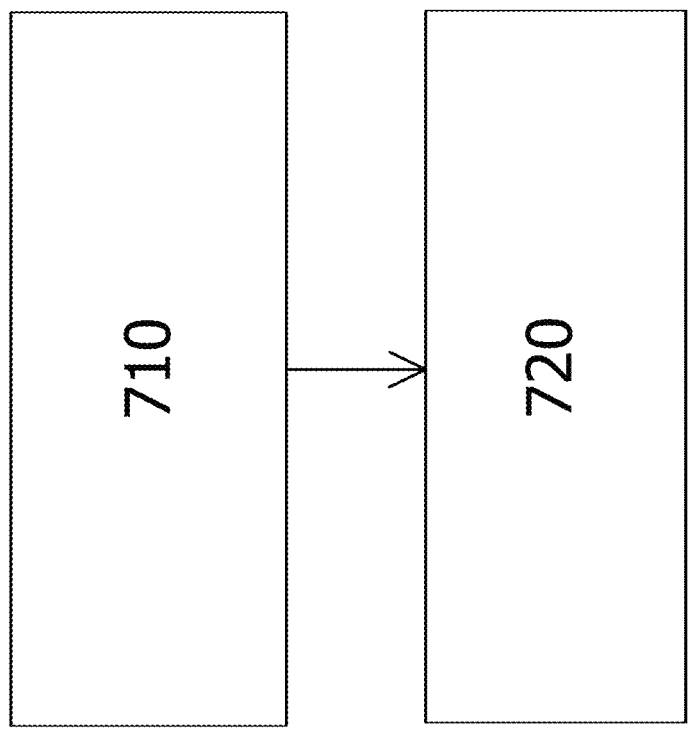
FIG. 7 shows a flowchart summarizing and generalizing an operation of the detector module, according to an embodiment.

FIG. 7 shows a flowchart 700 summarizing and generalizing an operation of the detector module 490, according to an embodiment. In step 710, the detector module 490 may be translated such that the point X of the detector module 490 moves along the curve 610 through movement rounds (i), i=1, . . . , M, with M being a positive integer, wherein the curve 610 is smooth. The curve 610 may be closed. In step 720, in the movement round (i), i=1, . . . , M, the detector module 490 may be used to capture partial images (i, j) of a scene, j=1, . . . , $H_i$, (e.g., the fourth, fifth, and sixth partial images for i=1) when the point X is at positions $P_{i,j}$ (e.g., the 3 positions P1, P2, and P3 of FIG. 6) on the curve 610, with $H_i$ being an integer greater than 1 (e.g., $H_1$=3 in FIG. 6).

In an embodiment, the 3 partial images captured in each movement round of the point X (e.g., the fourth, fifth, and sixth partial images captured in the first movement round) are such that it is possible to stitch the 3 partial images to form a single image of incident radiation. In an embodiment, the 3 partial images captured in each movement round of the point X (e.g., the fourth, fifth, and sixth partial images captured in the first movement round) may be stitched to form a single image of incident radiation.

In an embodiment, with reference to FIG. 6, the curve 610 may comprise a straight line segment A-B, wherein the $H_i$ positions (e.g., the positions P1, P2, and P3) are on the straight line segment A-B. In an embodiment, the detector module 490 may be translated such that the point X of the detector module 490 moves continuously (i.e., nonstop) along the curve 610 through the movement rounds (i), i=1, . . . , M. In other words, the point X does not stop during any of the movement rounds (i), i=1, . . . , M; and the point X does not stop between the movement rounds (i), i=1, . . . , M. in an embodiment, the velocity of the point X is a continuous function of time through the movement rounds (i), i=1, . . . , M.

In an embodiment, the partial image (i, j) may be captured when the point X is at the position $P_{i,j}$, in the movement round (i). For example, the fifth partial image mentioned above may be captured as follows. In the first movement round, while the point X moves from the position P1 to the position P2, charge carriers generated in the pixels 150 of the active areas 190*a* and 190*b* of the detector module 490 in response to incident radiation may be immediately drained. In an embodiment, this can be done by electrically connecting the electrical contacts 119B (FIG. 2A) of all pixels 150 to ground.

Next, in an embodiment, charge carriers generated in the pixels 150 of the active areas 190*a* and 190*b* of the detector module 490 in response to incident radiation may be gathered in the pixels 150 of the active areas 190*a* and 190*b* when the point X is at position P2. For example, charge carriers generated in the pixels 150 of the active areas 190*a* and 190*b* of the detector module 490 in response to incident radiation may be gathered in the pixels 150 of the active areas 190*a* and 190*b* for a pre-specified time period which may start when the point X starts to be at the position P2 in the first movement round. In an embodiment, the duration of the pre-specified time period may be inversely proportional to the speed of the point X on the curve 610 at the position P2 in the first movement round.

Next, in an embodiment, at the end of the pre-specified time period, the electrical signals in the pixels 150 resulting from the charge carriers gathered in the pixels 150 of the active areas 190*a* and 190*b* may be read out. These electrical signals constitute the fifth partial image. In an embodiment, the other partial images may be captured in a similar manner.

In the embodiments described above with reference to FIG. 5A-FIG. 5C and FIG. 6, the detector module 490 has 2 active areas 190*a* and 190*b*. In general, the detector module 490 may have any number of active areas 190 arranged in any way. In an embodiment, the detector module 490 may comprise active areas (similar to the active areas 190 of FIG. 3) arranged in K rows and L columns, wherein K and L are positive integers.

Figure 8A:
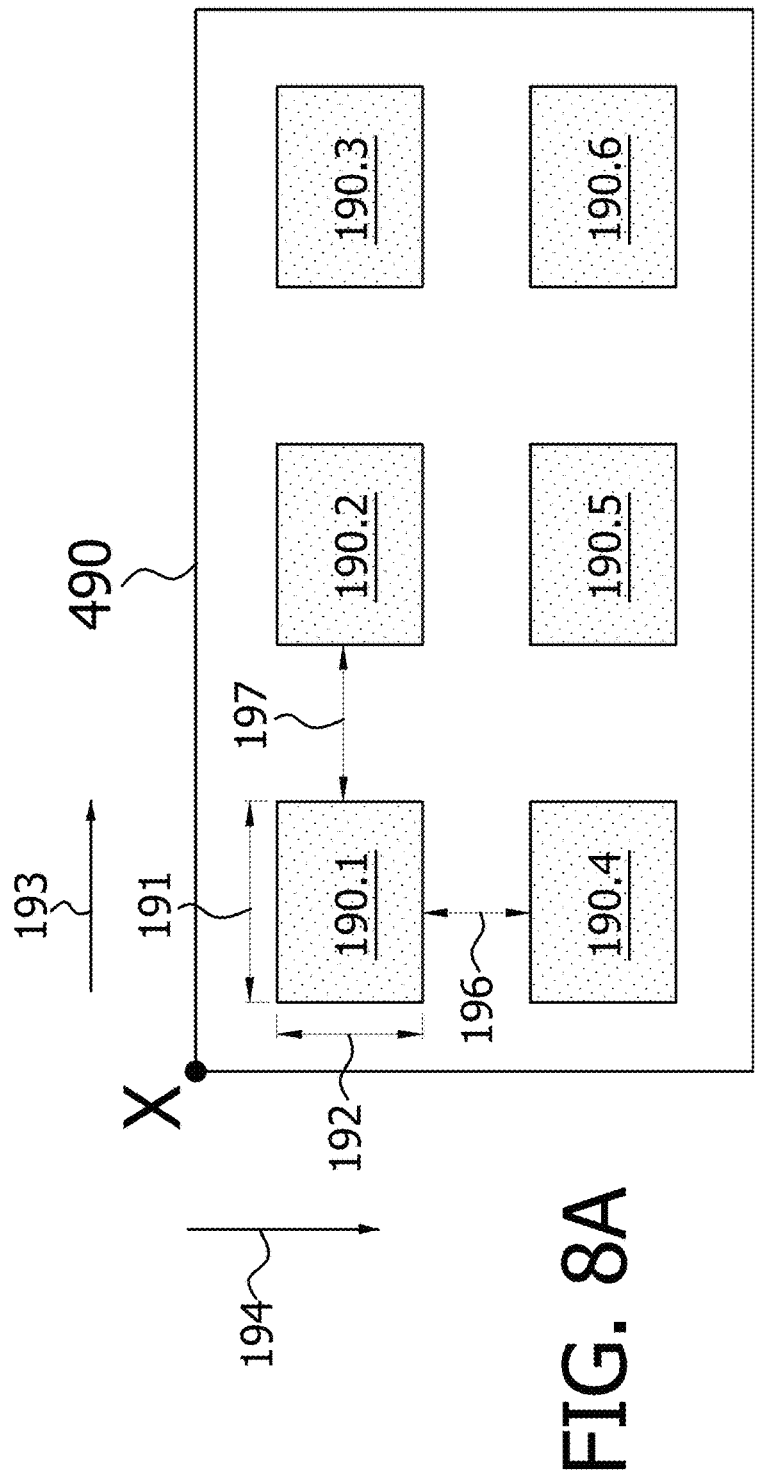
FIG. 8A-FIG. 8C show an operation of the detector module, according to an embodiment.

For example, with reference to FIG. 8A, the detector module 490 may comprise 6 active areas 190.1, 190.2, 190.3, 190.4, 190.5, and 190.6 (or 190.1-6 for short) arranged in 2 rows and 3 columns. In an embodiment, the active areas 190.1-6 may have the same size and shape. In an embodiment, the active areas 190.1-6 may have the shapes of rectangles. In an embodiment, the active areas 190.1-6 may be evenly arranged in the 2 rows and 3 columns.

In an embodiment, a size 191 in a row direction 193 (i.e., a direction parallel to a straight line going through the centers of the active areas of one of the rows) of the active area 190.1 may be greater than a distance 197 (edge-to-edge distance) between two neighboring active areas 190.1 and 190.2 of the top row. In an embodiment, a size 192 in a column direction 194 (i.e., a direction parallel to a straight line going through the centers of the active areas of one of the columns) of the active area 190.1 may be greater than a distance 196 (edge-to-edge distance) between two neighboring active areas 190.1 and 190.4 of the left column.

Figure 8B:
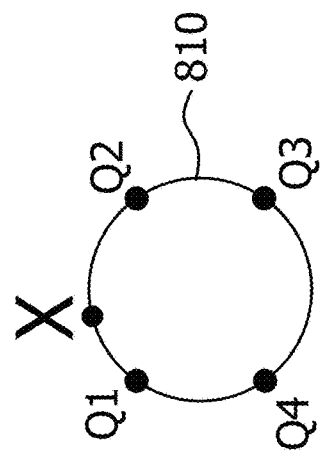

In an embodiment, with reference to FIG. 8A-FIG. 8B, the detector module 490 of FIG. 8A may be translated such that the point X of the detector module 490 moves along a curve 810 (FIG. 8B). In an embodiment, the curve 810 may be a circle. In an embodiment, the point X may move clockwise along the curve 810. In an embodiment, the point X may move continuously (i.e., nonstop) along the curve 810 through movement rounds of the point X.

In an embodiment, the four partial images captured by the 6 active areas 190.1-6 when the point X is at four positions Q1, Q2, Q3, and Q4 on the curve 810 in each of the movement rounds of the point X are such that it is possible to stitch the four partial images to form a single image. In an embodiment, the four partial images may be stitched to form a single image. In an embodiment, the 2 straight line segments Q1-Q2 and Q3-Q4 may be parallel to the row direction 193, and the 2 straight line segments Q2-Q3 and Q4-Q1 may be parallel to the column direction 194.

Figure 8C:
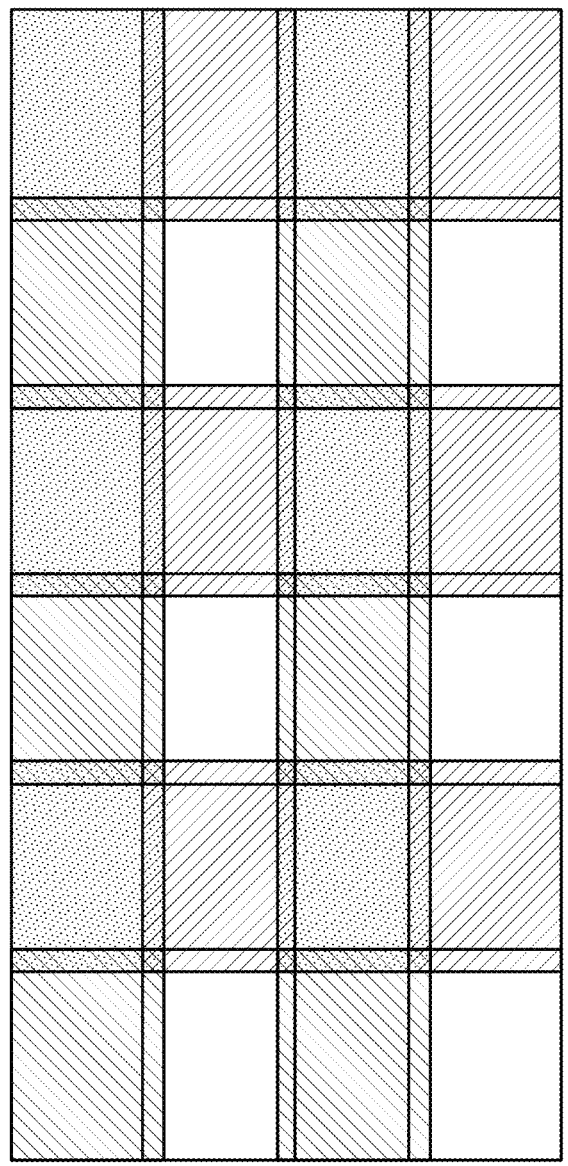

FIG. 8C shows 4 partial images captured by the 6 active areas 190.1-6 in one of the movement rounds of the point X (FIG. 8A-FIG. 8B), according to an embodiment. The partial image captured when the point X is at the position Q1 has stripes hatch pattern in south-west direction. The partial image captured when the point X is at the position Q2 has dots hatch pattern. The partial image captured when the point X is at the position Q3 has stripes hatch pattern in south-east direction. The partial image captured when the point X is at the position Q4 does not have any hatch pattern for simplicity.

Figure 9:
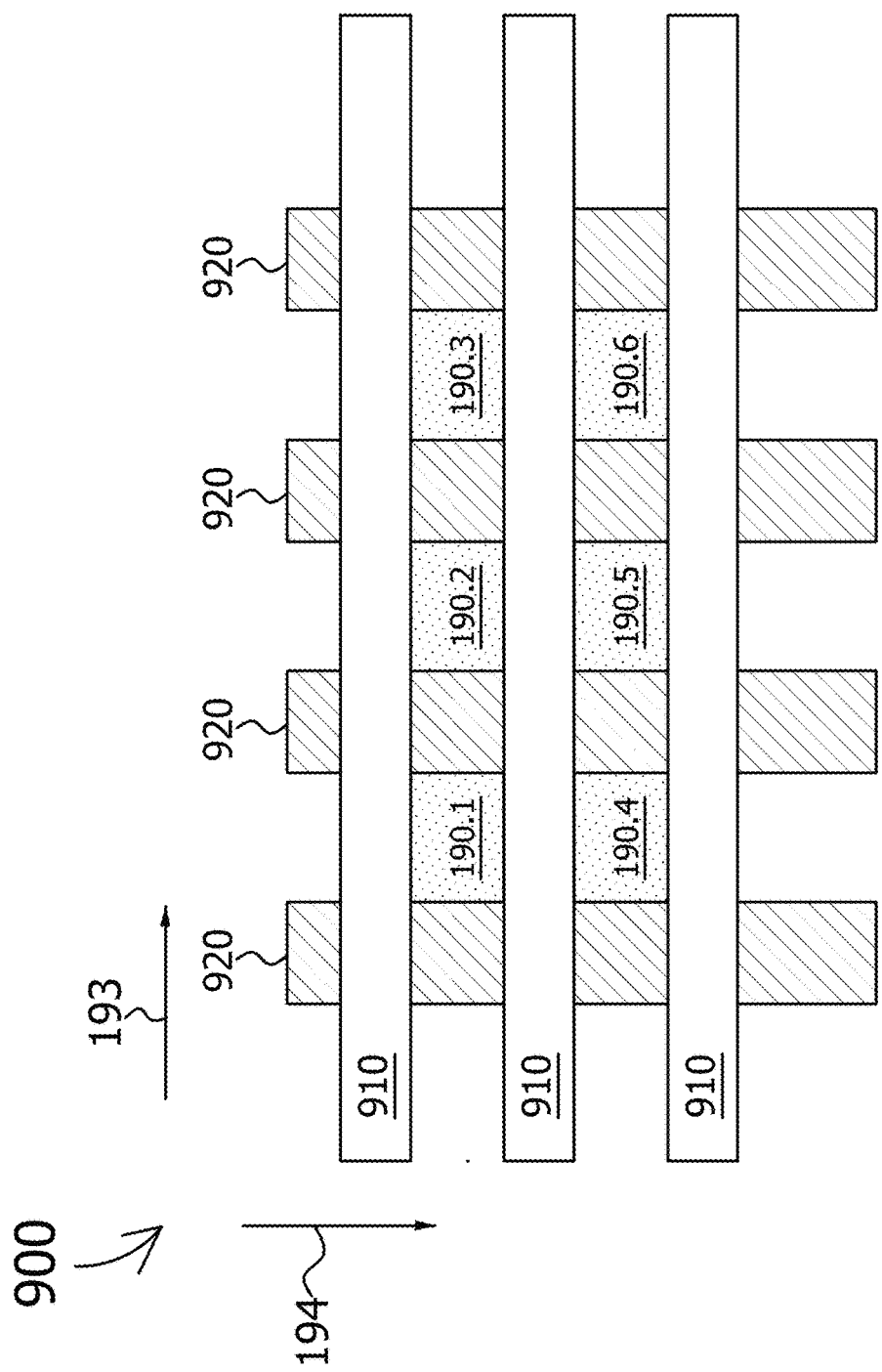
FIG. 9 schematically shows a top view of an imaging system, according to an embodiment.

FIG. 9 schematically shows a top view of an imaging system 900, according to an embodiment. Specifically, the imaging system 900 may comprise the detector module 490 of FIG. 8A and a shield system 910+920. In an embodiment, the detector module 490 may comprise the active areas 190.1-6 arranged in 3 rows and 2 columns as shown (other parts of the detector module 490 are not shown for simplicity). In an embodiment, the shield system 910+920 may comprise (A) row shield bars 910 extending in the row direction 193 (i.e., horizontally) and (B) column shield bars 920 extending in the column direction 194 (i.e., vertically).

In an embodiment, the shield system 910+920 may be moved such that the shield system 910+920 blocks radiation not targeting the active areas 190.1-6 while the point X of the detector module 490 is at the positions Q1, Q2, Q3, and Q4 (FIG. 8B) in the movement rounds of the point X. The shield system may be configured to translate the row shield bars 910 along the column direction, translate the column shield bars 920 along the row direction, or both. For example, while the point X moves clockwise along the curve 810 (FIG. 8B) from the position Q1 to the position Q2 in a movement round, the row shield bars 910 may remain stationary and the column shield bars 920 may be translated to the right (i.e., in the row direction 193) by a distance equal to the distance between Q1 and Q2. As a result, when a partial image is captured by the active areas 190.1-6 (when X is at Q2), the shield system 910+920 blocks radiation not targeting the active areas 190.1-6.

Next, similarly, while the point X moves clockwise along the curve 810 (FIG. 8B) from the position Q2 to the position Q3 in the same movement round, the column shield bars 920 may remain stationary and the row shield bars 910 may be translated down (i.e., in the column direction 194) by a distance equal to the distance between Q2 and Q3. As a result, when a partial image is captured by the active areas 190.1-6 (when X is at Q3), the shield system 910+920 blocks radiation not targeting the active areas 190.1-6.

Next, similarly, while the point X moves clockwise along the curve 810 (FIG. 8B) from the position Q3 to the position Q4 in the same movement round, the row shield bars 910 may remain stationary and the column shield bars 920 may be translated to the left (i.e., opposite to the row direction 193) by a distance equal to the distance between Q3 and Q4. As a result, when a partial image is captured by the active areas 190.1-6 (when X is at Q4), the shield system 910+920 blocks radiation not targeting the active areas 190.1-6.

Next, similarly, while the point X moves clockwise along the curve 810 (FIG. 8B) from the position Q4 to the position Q1 in the same movement round, the column shield bars 920 may remain stationary and the row shield bars 910 may be translated up (i.e., opposite to the column direction 194) by a distance equal to the distance between Q4 and Q1. As a result, when a partial image is captured (in the next movement round) by the active areas 190.1-6 (when X is at Q1), the shield system 910+920 blocks radiation not targeting the active areas 190.1-6.

In an embodiment, the row shield bars 910 may comprise a heavy metal such as copper. In an embodiment, the row shield bars 910 may be formed on a surface of a first substrate. The first substrate may comprise a semiconductor (e.g., silicon) which is not opaque to the radiation used for imaging. As a result, the row shield bars 910 may be translated by translating the first substrate.

In an embodiment, similarly, the column shield bars 920 may comprise a heavy metal such as copper. In an embodiment, the column shield bars 920 may be formed on a surface of a second substrate. The second substrate may comprise a semiconductor (e.g., silicon) which is not opaque to the radiation used for imaging. As a result, the column shield bars 920 may be translated by translating the second substrate.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method, comprising:
   translating a detector module such that a point of the detector module moves along a curve through movement rounds (i), i=1, . . . , M, with M being a positive integer, wherein the curve is smooth; and
   in the movement round (i), i=1, . . . , M, capturing partial images (i, j) of a scene using the detector module, j=1, . . . , $H_i$, when the point is at position $P_{i,j}$ on the curve, with $H_i$ being an integer greater than 1.

2. The method of claim 1, wherein the curve is a circle.

3. The method of claim 1,
   wherein the curve comprises a straight line segment, and wherein the positions $P_{i,j}$ are on the straight line segment.

4. The method of claim 1, wherein M≥2.

5. The method of claim 1, wherein the detector module comprises N spatially discontinuous active areas, N being a positive integer greater than 1.

6. The method of claim 1, wherein velocity of the point is a continuous function of time through the movement rounds (i), i=1, . . . , M.

7. The method of claim 1,
   wherein capturing partial image (i, j) comprises gathering charge carriers generated in detector module in response to incident radiation when the point is at position $P_{i,j}$ in the movement round (i).

8. The method of claim 1,
   wherein the detector module comprises N spatially discontinuous active areas arranged in K rows and L columns, with K, L, and N being positive integers, and wherein the K rows define a row direction and the L columns define a column direction.

9. The method of claim 8,
   wherein a size in the row direction of one of the N spatially discontinuous active areas is greater than a distance between two neighboring active areas of the N spatially discontinuous active areas in a row of the K rows, and
   wherein a size in the column direction of one of the N spatially discontinuous active areas is greater than a distance between two neighboring active areas of the N spatially discontinuous active areas in a column of the L columns.

10. The method of claim 8, further comprising operating a shield system such that the shield system blocks radiation not targeting the N spatially discontinuous active areas while the point is at the positions $P_{i,j}$, i=1, M and j=1, . . . , $H_i$.

11. The method of claim 10,
    wherein the shield system comprises (A) row shield bars extending in the row direction, and (B) column shield bars extending in the column direction,
    wherein operating the shield system comprises translating the row shield bars along the column direction, translating the column shield bars along the row direction, or both.

12. The method of claim 1, further comprising, for the movement round (i), forming an image (i) of an entirety of the scene by stitching the partial images (i, j), j=1, . . . , $H_i$.

13. The method of claim 1, wherein the curve is closed.

14. An imaging system, comprising a detector module,
    wherein the imaging system is configured to translate the detector module such that a point of the detector module moves along a curve through movement rounds (i), i=1, . . . , M, with M being a positive integer,
    wherein the curve is smooth, and
    wherein in the movement round (i), the detector module is configured to capture partial images (i, j) of a scene when the point is at positions $P_{i,j}$ on the curve, with $H_i$ being an integer greater than 1.

15. The imaging system of claim 14, wherein the curve is a circle.

16. The imaging system of claim 14,
    wherein the curve comprises a straight line segment, and wherein the $H_i$ positions are on the straight line segment.

17. The imaging system of claim 14, wherein M 2.

18. The imaging system of claim 14, wherein the detector module comprises N spatially discontinuous active areas, N being a positive integer greater than 1.

19. The imaging system of claim 14, wherein velocity of the point is a continuous function of time through the movement rounds (i), i=1, . . . , M.

20. The imaging system of claim 14,
    wherein, the detector module is configured to capture partial image (i, j) by gathering charge carriers generated in the detector module in response to incident radiation when the point is at position $P_{i,j}$.

21. The imaging system of claim 14,
    wherein the detector module comprises N spatially discontinuous active areas arranged in K rows and L columns, with K, L, and N being positive integers, and wherein the K rows define a row direction and the L columns define a column direction.

22. The imaging system of claim 21,
    wherein a size in the row direction of one of the N spatially discontinuous active areas is greater than a distance between two neighboring active areas of the N spatially discontinuous active areas in a row of the K rows, and wherein a size in the column direction of one of the N spatially discontinuous active areas is greater than a distance between two neighboring active areas of the N spatially discontinuous active areas in a column of the L columns.

23. The imaging system of claim 21, further comprising a shield system configured to block radiation not targeting the N spatially discontinuous active areas while the point is at the positions $P_{i,j}$, i=1, ..., M and j=1, ..., $H_i$.

24. The imaging system of claim 23,
wherein the shield system comprises (A) row shield bars extending in the row direction, and (B) column shield bars extending in the column direction,
wherein the shield system is configured to translate the row shield bars along the column direction, translate the column shield bars along the row direction, or both.

25. The imaging system of claim 14, further comprising a processor configured to, for the movement round (i), form an image (i) of an entirety of the scene by stitching the partial images (i, j), j=1, ..., $H_i$.

26. The imaging system of claim 14, wherein the curve is closed.

* * * * *